United States Patent
Khoury

(10) Patent No.: US 7,146,753 B2
(45) Date of Patent: Dec. 12, 2006

(54) ORTHOPEDIC DEVICE FOR DISTRIBUTING PRESSURE

(75) Inventor: M. Steven Khoury, 2370 Pond Valee, Oakland, MI (US) 48363

(73) Assignee: M. Steven Khoury, Oakland, MI (US)

( * ) Notice: Subject to any disclaimer, the term of this patent is extended or adjusted under 35 U.S.C. 154(b) by 0 days.

(21) Appl. No.: 11/336,209

(22) Filed: Jan. 20, 2006

(65) Prior Publication Data
US 2006/0112600 A1 Jun. 1, 2006

Related U.S. Application Data

(62) Division of application No. 10/756,611, filed on Jan. 13, 2004, now Pat. No. 7,020,990.

(51) Int. Cl.
A61F 5/14 (2006.01)
(52) U.S. Cl. .................... 36/154; 36/29; 12/146 M
(58) Field of Classification Search .................. 36/154, 36/29, 71, 43, 44, 155, 88, 93, 28; 12/142 N, 12/146 M
See application file for complete search history.

(56) References Cited

U.S. PATENT DOCUMENTS

| | | |
|---|---|---|
| 4,338,734 A | 7/1982 | Schwartz |
| 4,346,525 A | 8/1982 | Larsen et al. |
| 4,423,735 A | 1/1984 | Comparetto |
| 4,441,499 A | 4/1984 | Comparetto et al. |
| 4,470,782 A | 9/1984 | Zimmerman, Jr. et al. |
| 4,686,993 A | 8/1987 | Grumbine |
| 4,739,765 A | 4/1988 | Sydor et al. |
| 4,962,762 A | 10/1990 | Beekil |
| 5,027,801 A | 7/1991 | Grim |
| 5,042,100 A | 8/1991 | Bar et al. |
| 5,083,910 A | 1/1992 | Abshire et al. |
| 5,095,570 A | 3/1992 | Bar et al. |
| 5,163,237 A | 11/1992 | Rosen |
| 5,275,775 A | 1/1994 | Riecken |
| 5,311,680 A | 5/1994 | Comparetto |
| 5,316,545 A | 5/1994 | Cherubini |
| 5,463,824 A | 11/1995 | Barna |
| 5,540,982 A | 7/1996 | Scholz et al. |
| 5,611,153 A | 3/1997 | Fisher et al. |
| 5,728,169 A | 3/1998 | Norvell |
| 5,746,952 A | 5/1998 | Marshall |
| 5,768,803 A | 6/1998 | Levy |
| 5,843,483 A | 12/1998 | Theriault et al. |

(Continued)

FOREIGN PATENT DOCUMENTS

WO   WO 91/07152   5/1991

*Primary Examiner*—Ted Kavanaugh
(74) *Attorney, Agent, or Firm*—Brinks Hofer Gilson & Lione

(57) ABSTRACT

The present invention alleviates pain and discomfort from a limb of a patient by redistributing pressure on the limb. The present invention involves an orthopedic device for redistribution of pressure exerted on a limb of a patient. The device comprises a pressure-absorbing member and a breakable container disposed in the pressure absorbing member. The pressure absorbing member is contoured to cooperate with the shape of the limb. The pressure absorbing member has a pressure receiving cavity formed therein. The breakable container is disposed in the pressure receiving cavity and includes a reactant molding material. The breakable container has a predetermined elastic threshold to allow the breakable container to break at a high pressure area and to allow the reactant molding material to disperse from the high pressure area upon pressure exertion on the breakable container by the limb.

13 Claims, 6 Drawing Sheets

U.S. PATENT DOCUMENTS

| | | |
|---|---|---|
| 5,888,216 A | 3/1999 | Haberman |
| 5,896,677 A | 4/1999 | Barsorian |
| 5,958,546 A | 9/1999 | Mardix et al. |
| 6,012,726 A | 1/2000 | Grande et al. |
| 6,030,355 A | 2/2000 | Callinan et al. |
| 6,038,793 A | 3/2000 | Kendall |
| 6,086,551 A | 7/2000 | Allen |
| 6,092,314 A | 7/2000 | Rothbart |
| 6,110,134 A | 8/2000 | Clark, Jr. et al. |
| 6,170,177 B1 | 1/2001 | Frappier et al. |
| 6,173,511 B1 | 1/2001 | Perrault |
| 6,205,685 B1 | 3/2001 | Kellerman |
| 6,212,723 B1 | 4/2001 | Rothbart |
| 6,327,795 B1 | 12/2001 | Russell |
| 6,379,393 B1 | 4/2002 | Mavroidis et al. |
| 6,460,275 B1 | 10/2002 | Bennett et al. |
| 6,499,485 B1 | 12/2002 | Pepera |
| 6,510,626 B1 | 1/2003 | Greenawalt |
| 6,513,264 B1 | 2/2003 | Sinaie |
| 7,020,990 B1 * | 4/2006 | Khoury ................. 36/154 |
| 2004/0216330 A1 * | 11/2004 | Swigart ................. 36/29 |
| 2005/0166425 A1 * | 8/2005 | Seiter ................. 36/44 |

\* cited by examiner

ORTHOPEDIC DEVICE FOR DISTRIBUTING PRESSURE

CROSS-REFERENCE TO RELATED APPLICATIONS

This application is a divisional application and claims the benefit of U.S. non-provisional application Ser. No. 10/756,611, Jan. 13, 2004 now U.S. Pat. No. 7,020,990 and entitled "ORTHOPEDIC DEVICE FOR DISTRIBUTING PRESSURE," the entire contents of which are incorporated herein by reference.

BACKGROUND OF THE INVENTION

The present invention relates to an orthopedic device for redistribution of pressure exerted on a limb of a patient.

Orthopedic and podiatric devices are common and have been used for many years to treat patients with poor foot mechanics, insensitive foot, and foot pain. Foot specialists, such as podiatric and orthopedic surgeons, have treated such patients by prescribing shoe inserts and foot arch supports to alleviate pressure exerted on various areas of a foot of a patient. For example, shoe inserts and foot arch supports have been used to help patients undergoing podiatric therapy for plantar fasciitis. In many situations, a polyurethane foam shoe insert for cushion or support may alleviate a patient's foot discomfort.

However, in many other situations, a patient's discomfort may be more serious. For example, pressure or tension on a patient's foot may be directed on a pressure point or particular concentrated areas, including a metatarsal head, a metatarsal base, and a calcaneal tubercle of a foot of a patient. These concentrated areas may be referred to as high pressure points due to exerted pressure from weight or high stress activities. High pressure points may cause substantial discomfort to patients, risk of ulceration of the leg or foot and accelerated degeneration of fat pad of the foot.

Treatment for customized pressure relief on limbs, e.g. feet or prosthesis liners, is relatively time consuming and expensive. Typically, a customized shoe insert, orthotic or foot arch support is created by a foot specialist, orthotist or biomechanical lab. The process of creating a customized shoe insert typically involves a plaster cast of the foot or leg. The foot is generally casted in a "neutral position" or a relaxed position of the forefoot, mid-foot, and rear foot. From these casts, plaster is poured therein to produce a positive mold or impression of the patient's foot. The shoe insert is then constructed from the positive mold.

Although adequate, current ways of treating for the pressure relief of joints of the foot and distal leg pressure may be improved. Present methods correct static pressure of the foot or leg, but not dynamic pressure thereof.

Thus, there is a need for a more efficient, time saving device for treating patients with foot pain due to poor foot mechanics, insensitive foot and those with a decreased fat pad of the foot or leg.

BRIEF SUMMARY OF THE INVENTION

The present invention provides for an efficient, time saving device for treating patients having foot discomforts, insensitive foot, and decreased fat pad.

The present invention also provides for treating diabetic patients and those with an insensitive foot or leg. Disease processes render the foot and leg susceptible to additional complications due to altered neurological, orthopedic, and vascular complications. The present invention provides for a dynamic molding to relieve pressure points to allow for additional comfort and decrease the risk of ulcerations.

In one aspect, the present invention provides an orthopedic device for redistributing pressure exerted on a limb of a patient. In this embodiment, the device comprises a pressure absorbing member and a breakable container disposed in the pressure absorbing member. The pressure absorbing member is contoured to cooperate with the shape of the limb. The pressure absorbing member has a pressure receiving cavity formed therein. The breakable container is disposed in the pressure receiving cavity and includes a reactant molding material. The breakable container has a predetermined elastic threshold to allow the breakable container to break at a high pressure area and to allow the reactant molding material to disperse from the high pressure area upon pressure exertion thereon by the limb.

In another aspect, the present invention provides a method of redistributing pressure on a limb of a patient for orthopedic therapy. The method comprises providing a pressure absorbing member having a pressure receiving cavity formed therein and a breakable container disposed in the pressure receiving cavity. In this embodiment, the breakable container has a reactant molding material and a predetermined elastic threshold. The method further includes receiving pressure on the breakable container at the predetermined elastic threshold to define a high pressure area and dispersing the reactant molding material from the high pressure area. After curing, the reactant molding material forms a positive mold or impression of the patient's foot to redistribute the pressure on the limb.

Further objects, features and advantages of the invention will become apparent from consideration of the following description and the appended claims when taken in connection with the accompanying drawings.

DETAILED DESCRIPTION OF THE INVENTION

The present invention generally provides a customized orthopedic device for redistributing pressure exerted on a limb of a patient. In one embodiment, the orthopedic device hypogenically takes on the contours of the plantar side of a patient's limb, when placed in contact therewith and when pressure is exerted thereon. While avoiding a patient's potential allergic reaction to a molding material, the orthopedic device forms to the shape and contour of the patient's limb in a timely manner.

Figure 1:
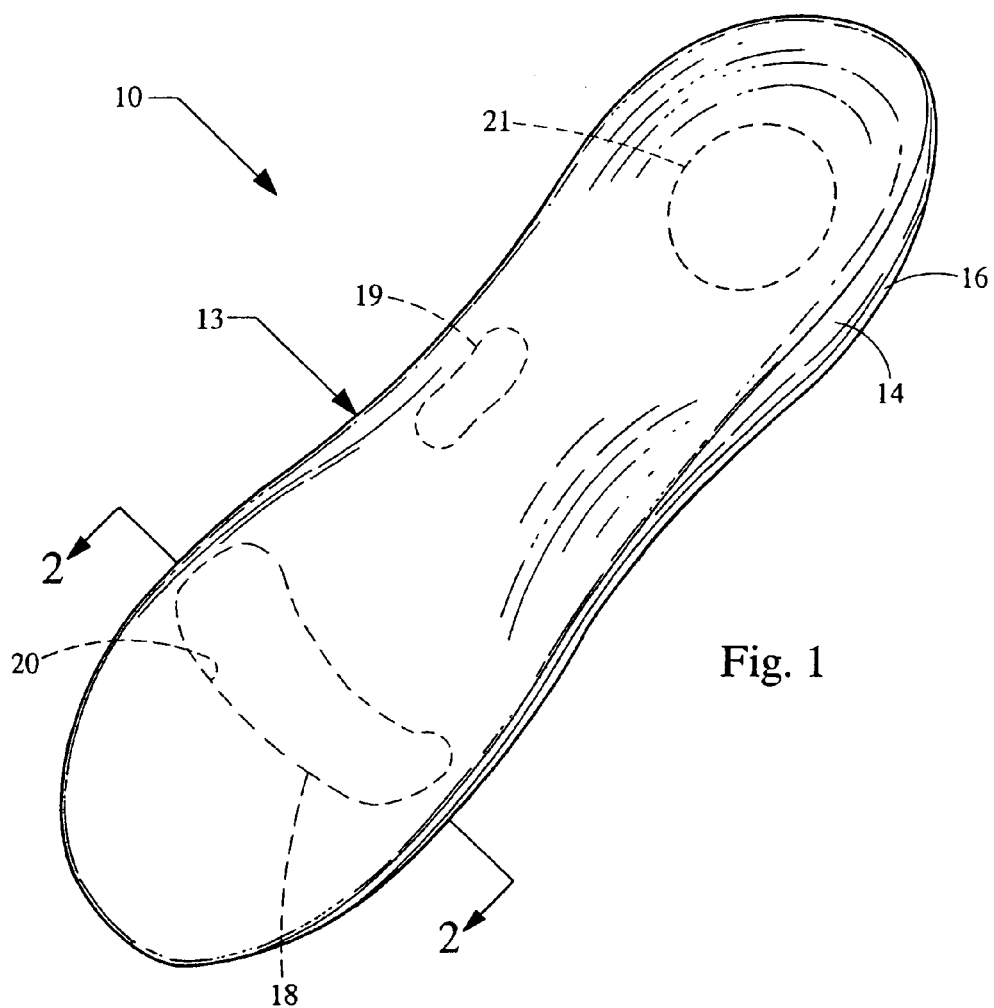
FIG. 1 is a perspective view of an orthopedic device in accordance with one embodiment of the present invention.

FIG. 1 illustrates a customized orthopedic device 10 in accordance with one embodiment of the present invention. As shown, the device 10 comprises a pressure absorbing member 13 having a contact layer 14 and a base layer 16 adhered to the contact layer 14 at its periphery. In this embodiment, the pressure absorbing member 13 is a shoe insert having a shape of a patient's foot to absorb pressure exerted by the foot of the patient. However, as described in greater detail below, it is to be understood that the pressure absorbing member may take on any other form to accommodate any limb of a patient.

The contact layer 14 may be comprised of Plastazote™, Poron™, Neoprene™, or any other suitable material. The base layer 16 may be injection molded or stamped with a cupped heal, arch pad, or metatarsal pad and may be made of any suitable material such as polyurethane. Plastazote™ is a high quality, light weight, closed cell polyethylene foam that is non-allergenic and may be used in direct contact with the skin. Plastazote™ is a heat moldable, grindable and washable material. Neoprene™ polychloroprene is a synthetic rubber. Poron™ is a micropourous polyurethane foam. The base layer and the contact layer may be adhered together by gluing or sonic welding or by any other suitable means.

Figure 2:
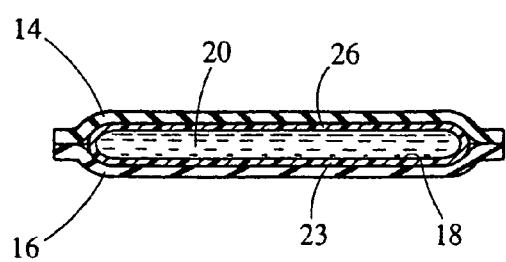
FIG. 2 is a cross-sectional side view of the orthopedic device taken along line 2—2 of FIG. 1.
Figure 3:
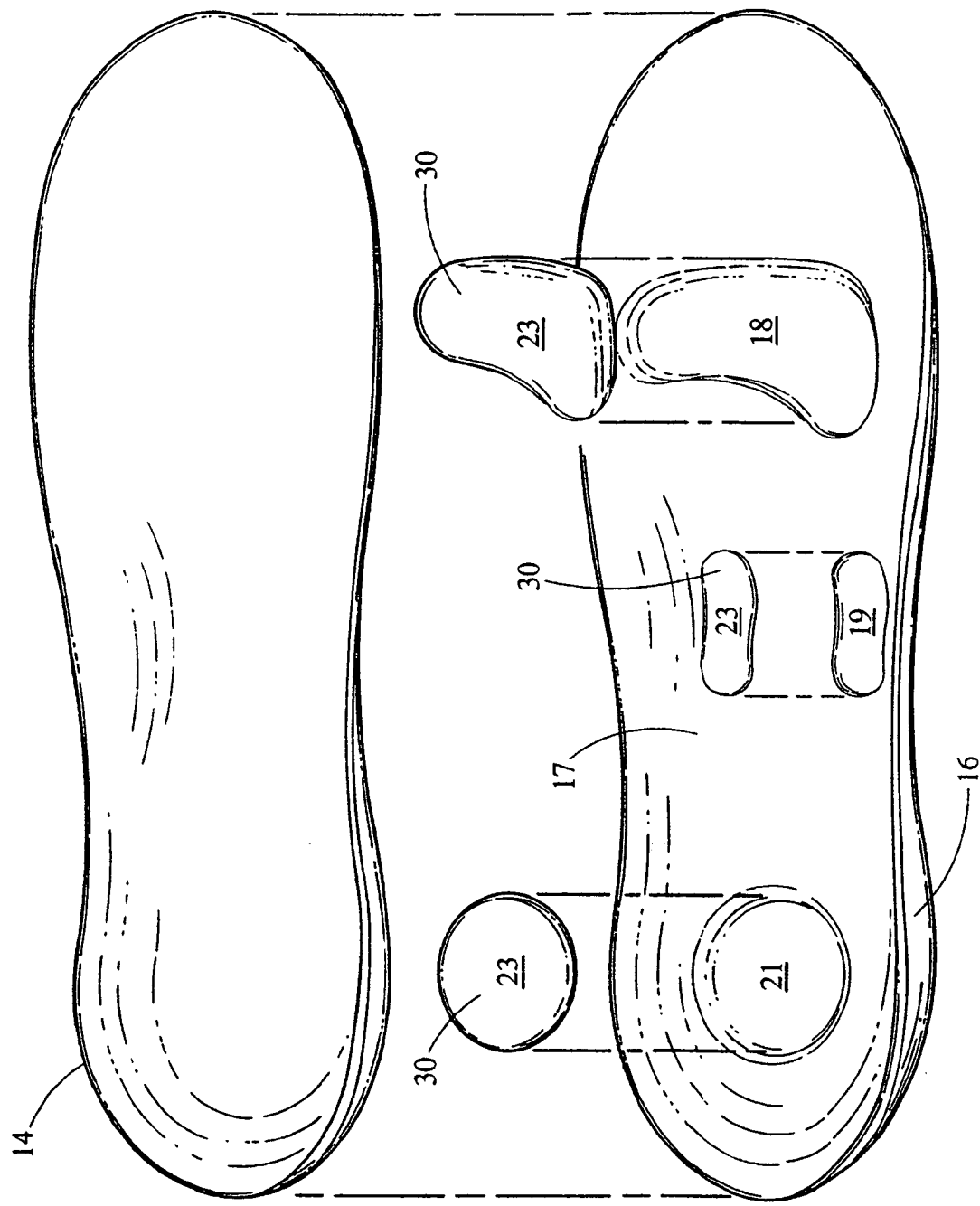
FIG. 3 is an exploded view of the orthopedic device of FIG. 1.

The pressure absorbing member 13 is contoured to cooperate with the limb of a patient. The contact layer 14 is configured to engage the limb of a patient. As shown in FIGS. 2 and 3, the base layer 16 includes an inner surface 17 having stress portions or openings 18, 19, 21 formed thereon. The contact layer 14 and the base layer 16 are aligned and cooperate with each other to form pressure receiving cavities 20 therebetween defined by the stress portions 18, 19, 21 of the base layer.

Device 10 further includes a breakable container 23 disposed in each pressure receiving cavity 20. Each breakable container 23 contains a reactant molding material, e.g., liquid latex or natural rubber and has a predetermined elastic threshold to allow the breakable container 23 to open or break at a high pressure area 30. The breaking of the breakable container 23 allows the reactant molding material 26 to be dispersed from the high pressure area 30 upon stress on the breakable container 23.

As the breakable container opens, the reactant molding material is dispersed to an area of lower pressure within the stress portion, thereby forming to the contour of the limb to form a positive mold or impression of the patient's foot. The reactant molding material is then allowed to cure and solidify to take on the contours of the limb. The reactant molding material provides greater surface area contact between the limb and the contact layer 14 at the high pressure area 30. As a result, the reactant molding material provides added support to the limb and redistributes pressure exerted thereon.

In this embodiment, each breakable container 23 has an elastic threshold to rupture or break the breakable container, thereby allowing the reactant molding material to be dispersed within the pressure receiving cavities. In this embodiment, the elastic threshold is defined by a rupture tension of about 15 pounds per square inch (psi). In another embodiment, the elastic threshold may be defined by a 10% stretch threshold of the material of the breakable container 23.

The predetermined elastic threshold may be determined by any suitable means to define a threshold at which the breakable container ruptures thereby allowing the reactant molding material to be dispersed within the respective pressure receiving cavities. For example, rupture tension (RT) may be provided as follows:

$$RT = \text{force per unit length},$$

wherein tension (T), pressure (P), and radius (r) are related by $$T = P \times r.$$

Using Young Modules of polyethylene as 1 megapascal and a thickness of sheet (d) of 0.5 millimeters (mm), T and strain are related by $$T = \text{modulus } (e) \times \text{thickness of sheet} \times 0.1 \text{ strain}.$$

Thus, $$T = \text{Young's modules} \times \frac{d}{r} \times 0.1 \text{ strain},$$

to provide $$\text{Rupture tension (RT)} = 0.1 \text{ megapascal} = 100 \text{ kilopascal} = 1 \text{ ATM} \approx 15 \text{ psi}.$$

Figure 4:
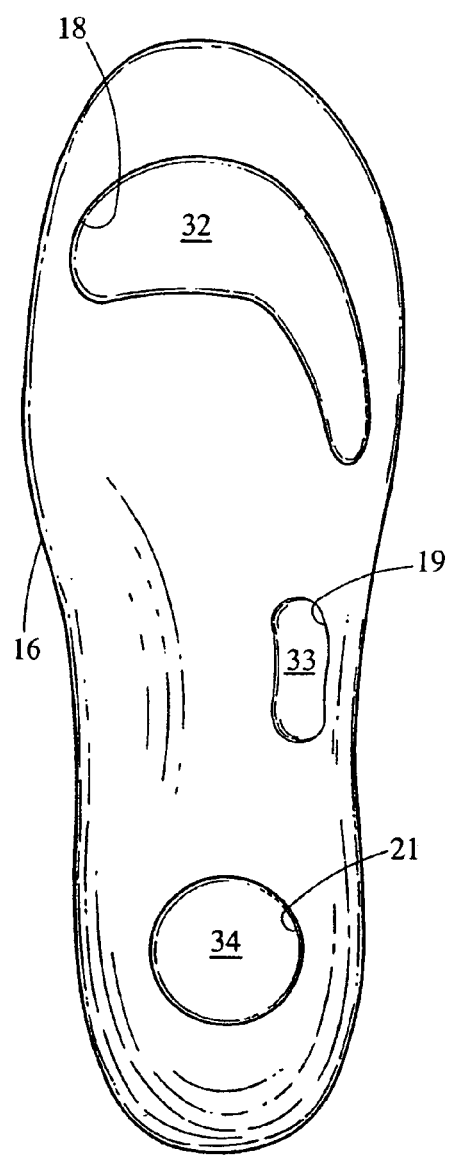
FIG. 4 is a plan view of a base layer of the orthopedic device in accordance with one embodiment of the present invention.

FIG. 4 illustrates one embodiment of the pressure absorbing member 13 of the orthopedic device 10. As shown, the stress portions 18, 19, 21 are formed at a rear foot portion 34, a mid-foot portion 33, and a fore-foot portion 32, respectively. As it can be seen, the rear foot portion is in alignment with the calcaneal tubercle of a patient's foot. The mid-foot portion 33 is in alignment with the fifth metatarsal base of a patient's foot. Moreover, the fore-foot portion 32 is in alignment with the first metatarsal head, the second metatarsal head, the third metatarsal head, the fourth metatarsal head, and the fifth metatarsal head of a patient's foot.

Figure 5:
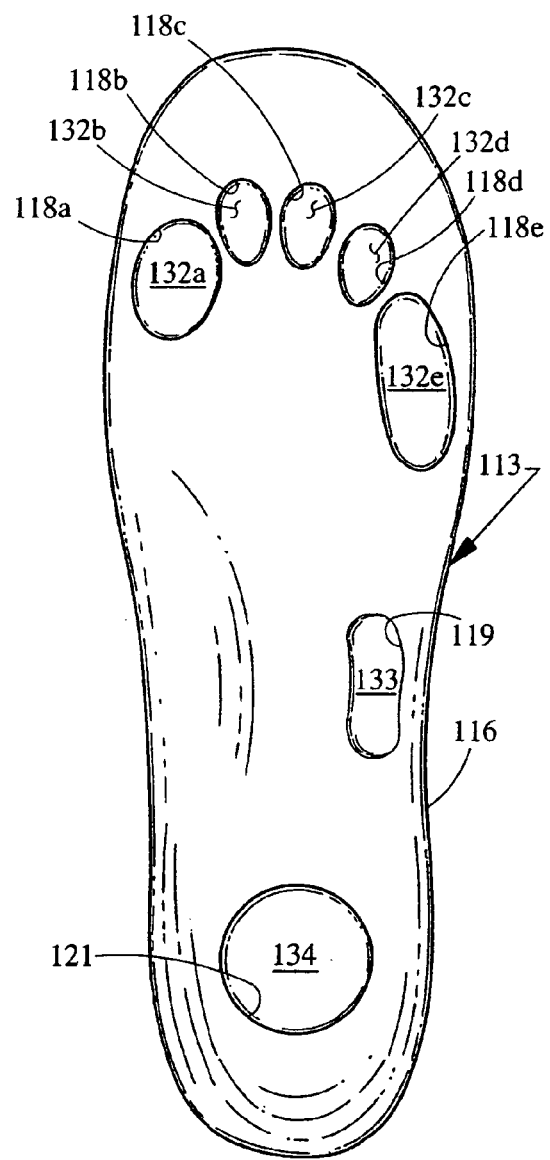
FIG. 5 is a plan view of a base layer of the orthopedic device in accordance with another embodiment of the present invention.

In this embodiment, the fore-foot portion 32, the mid-foot portion 33, and the rear foot portion 34 are formed along a separate stress portion and pressure receiving cavity of the pressure absorbing member. However, it is to be understood that each stress portion may be formed in any other suitable manner. For example, as shown in another embodiment depicted as reference numeral 116 in FIG. 5, the fore-foot portion of the pressure absorbing member includes five separate stress portions 118a–118e, one of each being in alignment with the first metatarsal head, the second metatarsal head, the third metatarsal head, the fourth metatarsal head, and the fifth metatarsal head of a patient's foot. Thus, in this embodiment, the device 110 includes a plurality of breakable containers in fore-foot portions 132a–132e.

The breakable container may be configured to rupture at any suitable location thereon to allow the reactant molding material to be dispersed within the respective pressure receiving cavity of the device. The breakable container may be made of a low density polymer, e.g., low density polyethylene or low density polypropylene More specifically, as shown in FIG. 4, the base layer 16 further includes stress portion 19 formed thereon and located at the mid-foot portion 33. The mid-foot portion 33 may be referred to as a fifth metatarsal base portion which, in use, is in alignment with the fifth metatarsal base of a patient's foot. Moreover, the base layer 16 further includes stress portion 21 formed thereon and located at the rear foot portion 34. The rear foot portion may be referred to as a calcaneal tubercle portion which, in use, is in alignment with the calcaneal tubercle of a patient's foot. Breakable containers containing the reactant molding material are also disposed in the mid-foot portion and the rear foot portion of the pressure receiving cavity of the base layer.

Figure 6:
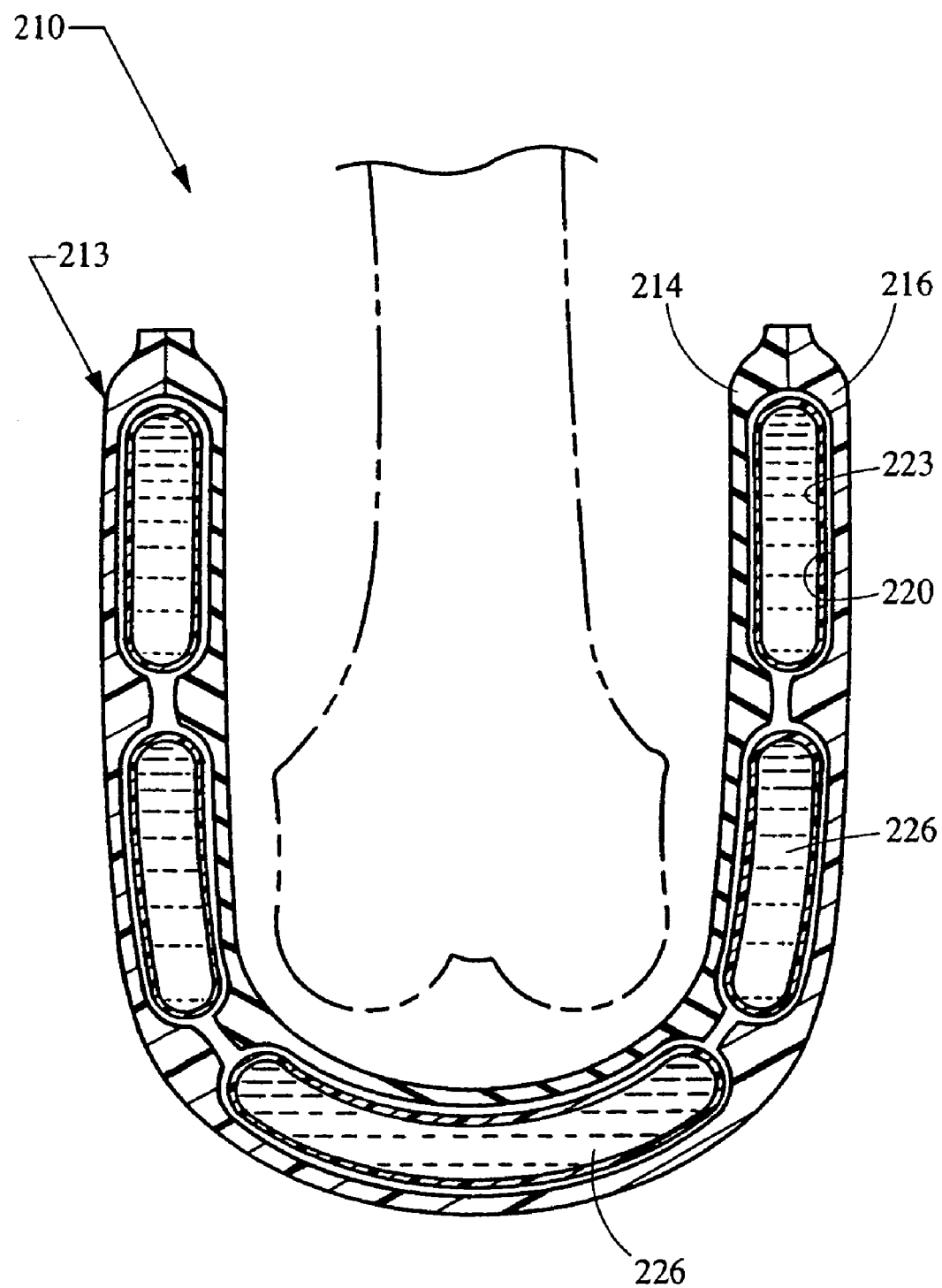
FIG. 6 is a cross-sectional view of an orthopedic device in accordance with still another embodiment of the present invention.

FIG. 6 illustrates orthopedic device 210 having similar components as orthopedic device 10 described above. However, rather than having a peripheral shape of a foot of a patient, device 210 takes on a peripheral shape of a proximal end of a prosthesis and on a limb stump. For example, orthopedic device 210 may take on a shape to cooperate with the proximal end of a prosthetic leg 213 of a patient, thereby engaging the end of the prosthetic limb and receiving the limb of the patient. As shown, device 210 may comprise a pressure absorbing member 213 having a contact layer 214 and a base layer 216 peripherally adhered to the contact layer 214, similar to the pressure absorbing member 13, contact layer 14, and base layer 16 of the device 10.

FIG. 6 further illustrates a plurality of breakable containers 223 disposed within pressure receiving cavities 220 of the pressure absorbing member. Device 210 may be configured to receive distal ends of a femur stump or a tibia or fibula stump of a patient. Moreover, it is to be understood that formation of the stress portions, the pressure receiving cavities, and the location of the high pressure areas may vary and would not fall beyond the scope or spirit of the present invention.

In use, the orthopedic device redistributes pressure on a limb of a patient for orthopedic therapy. The breakable container receives pressure from the limb of the patient. At the predetermined elastic threshold of the breakable container, the reactant molding material is dispersed from the high pressure area to the pressure receiving cavities. After curing, the reactant molding material defines a positive mold or impression of the patient's foot to alleviate pain and discomfort.

Figure 7:
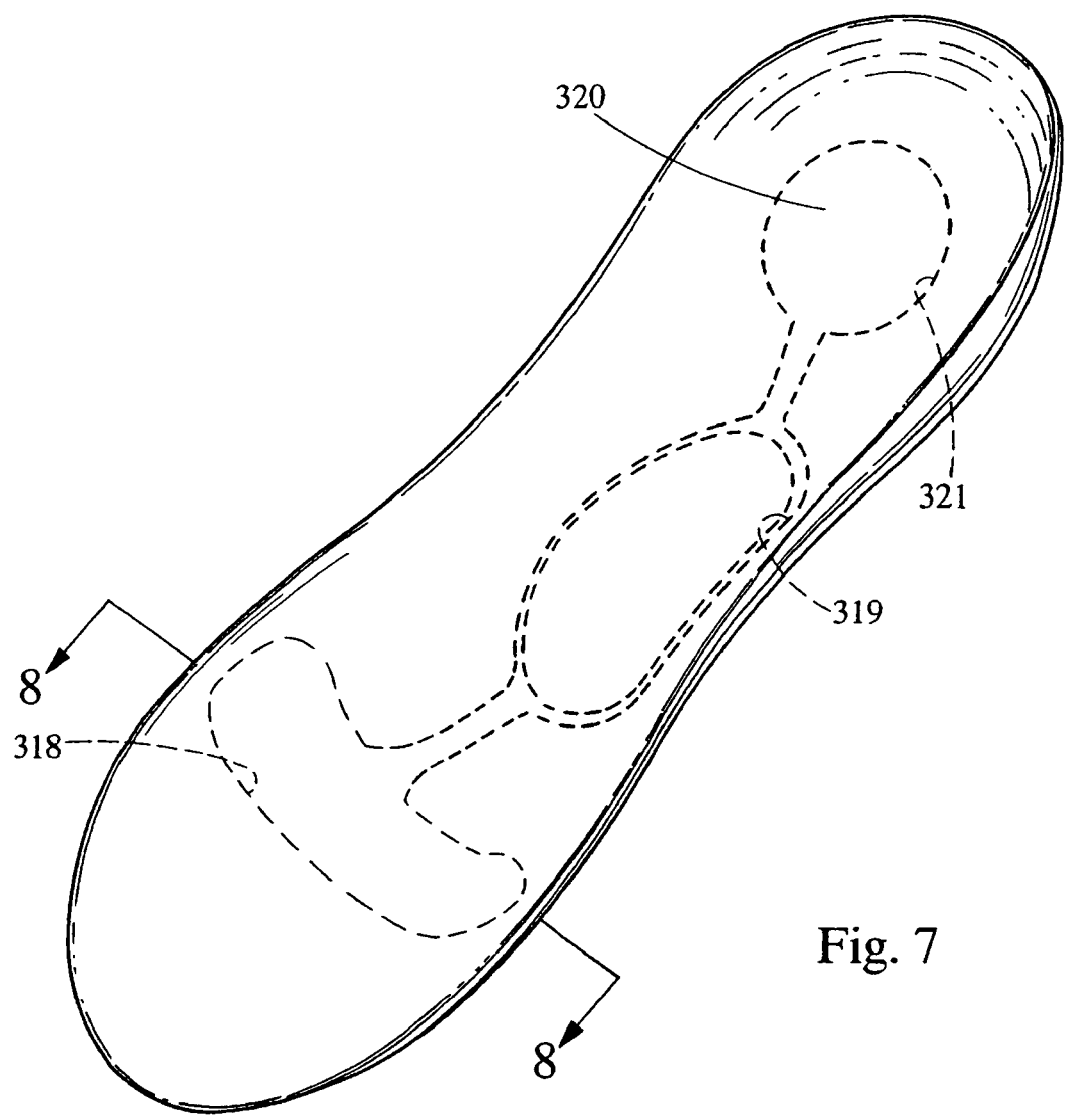
FIG. 7 is a plan view of an orthopedic device in accordance with yet another embodiment of the present invention.
Figure 8:
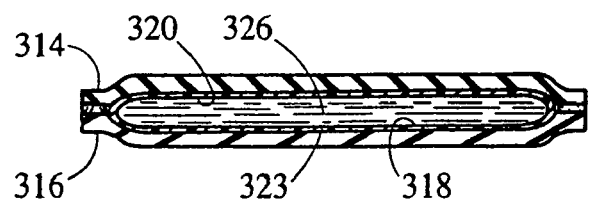
FIG. 8 is a cross-sectional view of the orthopedic device taken along line 8—8 of FIG. 7.
Figure 9:
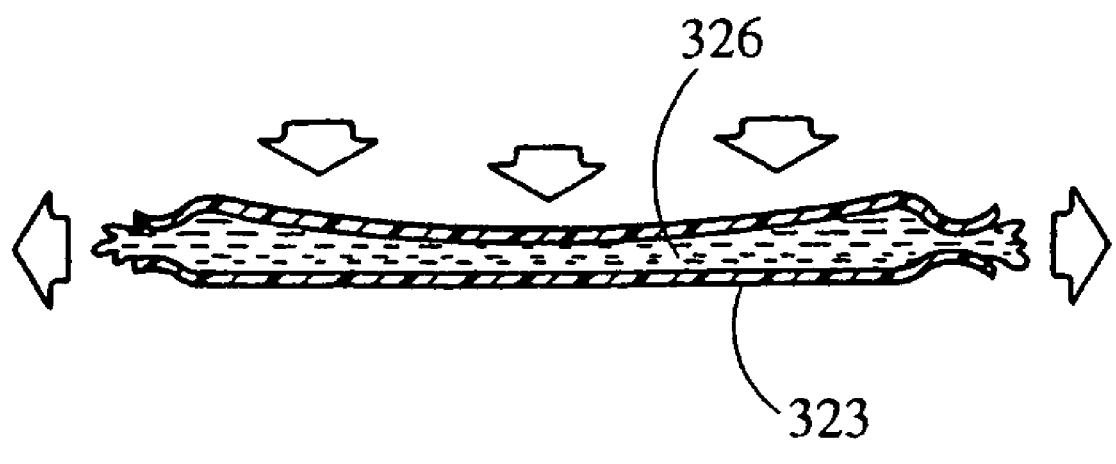
FIG. 9 is a cross-sectional view of the orthopedic device dispersing a reactant molding material.

FIGS. 7–9 depict another embodiment of the present invention. As shown, orthopedic device 310 includes similar components as the device 10 in FIG. 1. For example, device 310 may comprise a pressure absorbing member 313 having a contact layer 314 and a base layer 316 peripherally adhered to the contact layer 314, similar to the pressure absorbing member 13, contact layer 14, and base layer 16 of the device 10. In this embodiment, the pressure absorbing member 313 comprises a heat sensitive breakable container 323 including the reactant molding material and having one-way valves 327 through which the reactant molding material 326 may exit. The breakable container 323 is configured to selectively degrade or rupture at a predetermined temperature and at pressure points where the one-way valves 327 are disposed. Preferably, the breakable container 323 is disposed in stress portion 319 of pressure absorbing member 313. As shown, stress portion 319 is formed adjacent the arch of the foot of a patient. Since the arch portion of the foot is a relatively low pressure area of a patient's foot, the breakable container 323 will not be ruptured during normal use at temperatures below the predetermined temperature.

However, when placed in a heat source, e.g., an oven, at or above the predetermined temperature, heat sensitive breakable container 323 will selectively rupture at the pressure points at which the one-way valves are disposed, thereby allowing the reactant molding material to exit therefrom. Pressure applied from the patient's foot then will cause the reactant molding material to disperse or flow to stress portions 318 and 321 of the pressure absorbing member 313 while avoiding backflow back to stress portion 319.

As mentioned, the heat sensitive breakable container 323 is comprised of material configured to rupture or degrade at a predetermined temperature. The predetermined temperature may be preferably greater than 100° F., more preferably greater than 120° F., and most preferably greater than 140° F. The material may be a polymeric material such as low density polyethylene, linear-low density polyethylene, polypropylene, or any other suitable material.

The one-way valves may be constructed by any suitable means onto the breakable containers such that the reactant molding material may be dispersed to the pressure receiving cavities.

In use, the orthopedic device depicted in FIGS. 7–9 redistributes pressure on a limb of a patient for orthopedic therapy. In this embodiment, the pressure absorbing member is heated to the predetermined temperature threshold defining a high temperature area of the breakable container. Pressure placed on the device from the patient's limb forces the reactant molding material to the stress portions. After drying, the reactant molding material produces a positive mold or impression of the patient's foot, thereby redistributing the pressure on the limb and alleviating pain on the foot.

While the present invention has been described in terms of preferred embodiments, it will be understood, of course, that the invention is not limited thereto since modifications may be made to those skilled in the art, particularly in light of the foregoing teachings.

The invention claimed is:

1. An orthopedic device for redistribution of pressure exerted on a limb of a patient, the device comprising:
   a pressure absorbing member contoured to cooperate with the shape of the limb, the pressure absorbing member having a plurality of pressure receiving cavities formed therein; and
   a breakable container disposed in one of the pressure receiving cavities and including a reactant molding material, the breakable container having a predetermined temperature threshold to allow the breakable container to break at a high temperature area and the reactant molding material to disperse from the high temperature area upon heat on the breakable container beyond the predetermined temperature threshold.

2. The device of claim 1 wherein the pressure receiving cavities are formed at a rear foot portion, a mid-foot portion, and a forefoot portion.

3. The device of claim 2 wherein the rear foot portion is in alignment with one of the medial tubercle or lateral tubercle of the calcaneal tubercle of the patient.

4. The device of claim 2 wherein the mid-foot portion is in alignment with the fifth metatarsal base of the patient.

5. The device of claim 2 wherein the fore-foot portion is in alignment with the first metatarsal head, the second metatarsal head, the third metatarsal head, the fourth metatarsal head, and the fifth metatarsal head of the patient.

6. The device of claim 1 wherein the breakable container is made of a low density polymer.

7. The device of claim 1 wherein the reactant molding material is made of latex.

8. The device of claim 1 wherein the pressure absorbing member includes:
   a contact layer for engaging the limb of the patient; and
   a base layer including an inner surface having a stress portion formed thereon, the base layer being aligned with the top layer and cooperating therewith to form the pressure receiving cavity adjacent the stress portion.

9. The device of claim 1 wherein the pressure absorbing member includes:
a base layer; and
a top layer for engaging the limb of the patient, the top layer including an inner surface having a pressure receiving portion formed thereon, the top layer being lined with the base layer and cooperating therewith to form the pressure receiving cavity at the pressure receiving portion.

10. The device of claim 1 wherein the predetermined temperature threshold is greater than 100° Fahrenheit.

11. The device of claim 1 wherein the predetermined temperature threshold is greater than 120° Fahrenheit.

12. The device of claim 1 wherein the predetermined temperature threshold is greater than 140° Fahrenheit.

13. A method of redistributing pressure on a limb of a patient for orthopedic therapy, the method comprising:
providing a pressure absorbing member having a pressure receiving cavity formed therein and a breakable container disposed in the pressure receiving cavity, the breakable container having a reactant molding material and a predetermined temperature threshold;
heating the pressure absorbing member to the predetermined temperature threshold to define a high temperature area of the breakable container; and
dispersing the reactant molding material from the high temperature area to redistribute the pressure on the limb.

* * * * *